United States Patent
Higgins et al.

(10) Patent No.: US 9,167,356 B2
(45) Date of Patent: Oct. 20, 2015

(54) ELECTROOCULOGRAM AS A CONTROL IN A HEARING ASSISTANCE DEVICE

(71) Applicant: Starkey Laboratories, Inc., Eden Prairie, MN (US)

(72) Inventors: Sidney A. Higgins, Maple Grove, MN (US); James R. Newton, Burnsville, MN (US); Peter Salmi, Mound, MN (US)

(73) Assignee: Starkey Laboratories, Inc., Eden Prairie, MN (US)

( * ) Notice: Subject to any disclaimer, the term of this patent is extended or adjusted under 35 U.S.C. 154(b) by 0 days.

(21) Appl. No.: 13/739,928

(22) Filed: Jan. 11, 2013

(65) Prior Publication Data

US 2014/0198936 A1 Jul. 17, 2014

(51) Int. Cl.
  *H04R 25/00* (2006.01)
  *G06F 3/01* (2006.01)
  *A61B 3/113* (2006.01)
  *A61B 5/0496* (2006.01)

(52) U.S. Cl.
  CPC ............... *H04R 25/40* (2013.01); *G06F 3/013* (2013.01); *A61B 3/113* (2013.01); *A61B 5/0496* (2013.01); *H04R 25/407* (2013.01); *H04R 25/552* (2013.01); *H04R 2225/61* (2013.01)

(58) Field of Classification Search
  USPC .................................................. 381/313, 327
  See application file for complete search history.

(56) References Cited

U.S. PATENT DOCUMENTS

2010/0074460 A1* 3/2010 Marzetta ........................ 381/313
2011/0096941 A1   4/2011 Marzetta et al.

* cited by examiner

*Primary Examiner* — Davetta W Goins
*Assistant Examiner* — Amir Etesam
(74) *Attorney, Agent, or Firm* — Schwegman Lundberg & Woessner, P.A.

(57) ABSTRACT

Disclosed herein, among other things, are systems and methods for controlling operation of a hearing assistance device. One aspect of the present subject matter includes a method of operating a hearing assistance device worn by a wearer. The method includes tracking eye movements of the wearer using a sensor on or in the hearing assistance device to obtain an electrooculogram (EOG). At least one parameter of the hearing assistance device is adjusted using the EOG, according to various embodiments.

27 Claims, 6 Drawing Sheets

ELECTROOCULOGRAM AS A CONTROL IN A HEARING ASSISTANCE DEVICE

TECHNICAL FIELD

This document relates generally to hearing assistance systems and more particularly to an electrooculogram (EOG) as a control in a hearing assistance device.

BACKGROUND

Modern hearing assistance devices, such as hearing aids, typically include digital electronics to enhance the wearer's listening experience. Hearing aids are electronic instruments worn in or around the ear that compensate for hearing losses by specially amplifying sound. Hearing aids use transducer and electro-mechanical components which are connected via wires to the hearing aid circuitry.

Hearing aids typically require conspicuous movement or interaction on the user's part to input commands into the hearing aid in order to influence an outcome or performance. This input is typically done by using a pushbutton located on the device or in more sophisticated units, the pressing of a button on a wireless remote. Cycling thru memory presets, adjusting directional control, or simply adjusting the volume draws attention to the fact that the user is wearing a hearing device.

Accordingly, there is a need in the art for improved systems and methods for controlling operation of a hearing assistance device.

SUMMARY

Disclosed herein, among other things, are systems and methods for controlling operation of a hearing assistance device. One aspect of the present subject matter includes a method of operating a hearing assistance device worn by a wearer. The method includes tracking eye movements of the wearer using a sensor on or in the hearing assistance device to obtain an electrooculogram (EOG). At least one parameter of the hearing assistance device is adjusted using the EOG, according to various embodiments.

One aspect of the present subject matter includes a hearing assistance system for a wearer. In various embodiments, the system includes at least one sensor on or in a hearing assistance device worn by the wearer, the electrode configured to track movements of the wearer's eyes to obtain an electrooculogram (EOG). A controller in the hearing assistance device is configured to adjust at least one parameter of the hearing assistance device using the EOG, in various embodiments.

This Summary is an overview of some of the teachings of the present application and not intended to be an exclusive or exhaustive treatment of the present subject matter. Further details about the present subject matter are found in the detailed description and appended claims. The scope of the present invention is defined by the appended claims and their legal equivalents.

DETAILED DESCRIPTION

The following detailed description of the present subject matter refers to subject matter in the accompanying drawings which show, by way of illustration, specific aspects and embodiments in which the present subject matter may be practiced. These embodiments are described in sufficient detail to enable those skilled in the art to practice the present subject matter. References to "an", "one", or "various" embodiments in this disclosure are not necessarily to the same embodiment, and such references contemplate more than one embodiment. The following detailed description is demonstrative and not to be taken in a limiting sense. The scope of the present subject matter is defined by the appended claims, along with the full scope of legal equivalents to which such claims are entitled.

The present detailed description will discuss hearing assistance devices using the example of hearing aids. Hearing aids are only one type of hearing assistance device. Other hearing assistance devices include, but are not limited to, those in this document. It is understood that their use in the description is intended to demonstrate the present subject matter, but not in a limited or exclusive or exhaustive sense.

Hearing aids typically require conspicuous movement or interaction on the user's part to input commands into the hearing aid in order to influence an outcome or performance. This input is typically done by using a pushbutton located on the device or in more sophisticated units, the pressing of a button on a wireless remote. Cycling thru memory presets, adjusting directional control, or simply adjusting the volume draws attention to the fact that the user is wearing a hearing device. Previously, controlling a hearing assistance device to change a function or parameter involved pushbuttons located on the device, remote control units, capacitive sensors, ultrasonic interfaces, pressure or feedback switches, infrared sensors, or accelerometers. These previous methods have several disadvantages. For example, reaching up to the device or into a pocket to find the proper button on remote causes the wearer to be distracted from that which they are trying to hear. In the case of the remote control, a separate battery and device must be present and maintained. In addition, a button placed on a hearing aid is an opportunity for moisture ingress, as every seam line or opening in the case results in a degradation of reliability. Capacitive sensors are prone to false actuation in the presence of moisture. Ultrasonic sensors are electrically noisy and can disrupt other circuit operation. Infrared sensors are blocked by hair and often cannot be located conveniently. Accelerometers require conspicuous movement to operate.

Figure 1A:
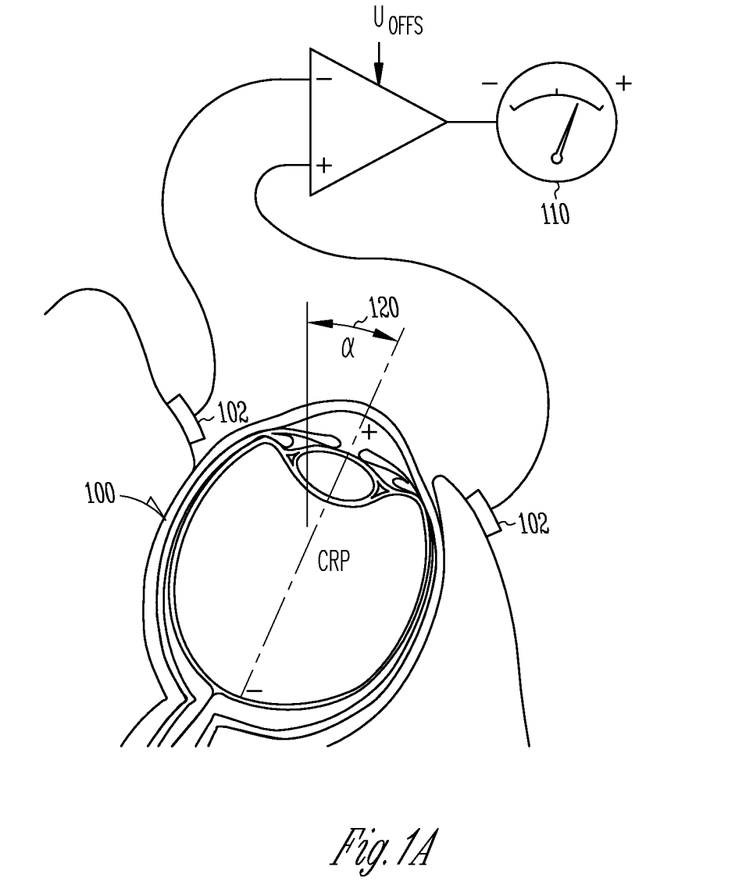
FIG. 1A illustrates a system used to obtain an electrooculogram (EOG).

An electrooculogram (EOG) is a recording of eye movement and eye position provided by a difference in electrical potential between two electrodes. Currently, EOGs require addition of facial worn elements like electrodes or cameras to capture eye movement. FIG. 1A illustrates a system used to obtain an electrooculogram (EOG). The human eye 100 is polarized, with the front or corneal-side of the eye being positive and the back or retinal side being negative (due to the rich concentration of negatively charged nerve endings there). A pair of electrodes 102 placed in the horizontal plane will detect left-right movements. The measured potential 110 in either direction is proportional to the amount of eye rotation 120.

Disclosed herein, among other things, are systems and methods for controlling operation of a hearing assistance device. One aspect of the present subject matter includes a method of operating a hearing assistance device worn by a wearer. The method includes tracking eye movements of the wearer using a sensor, such as an electrode, on or in the hearing assistance device to obtain an electrooculogram (EOG). At least one parameter of the hearing assistance device is adjusted using the EOG, according to various embodiments.

The present subject matter uses an EOG to provide a control means for hearing aid. In various embodiments, switching or proportional control of some aspect of hearing aid operation is be managed by left-to-right eye movement. In-situ EOG as a means of user interface or directional control will result in greater user satisfaction for hearing aid wearers. There is nothing for the wearer to carry, find, manipulate or maintain. In various embodiments, by simply looking in a direction binaural beam-forming can be directed or, with a simple pattern of eye movements volume or memory presets can be cycled.

An EOG provides a relatively large signal, which provides an advantage for detection of the signal. Specifically, a relatively low amplification and filtering, and hence a low power, can be used for detection. Hearing assistance devices, in which space and power are limited, can accommodate the detection of EOG signals in various embodiments. EOG technology depends upon detecting electric field changes due to charge differentials on each eyeball. By placing EOG electrodes in the ear canal or on the ear as part of a hearing assistance device, a wearer's eye movement can be precisely detected and those movements are used to control desired functions of the hearing device. As the wearer looks to the left or the right, the charge shifts in the space between the users ears—a charge that can be detected by appropriate sensors on or in the hearing assistance device. In various embodiments, by mapping types of eye movements a desired outcome could be incorporated, for example Saccade and fixations. In one embodiment, eye movements are characterized, such as pausing over text, and a function is created that allows the device to self-mute when the wearer is reading in a noisy room and return to normal setting when they stop.

Using an EOG involves detecting a charged object (the cornea) moving closer to or away from a detector, so no ohmic contact is needed in the form of dermal electrodes, and the moving charge can be detected electrostatically in an embodiment. One embodiment uses remote electrostatic detection capable of discerning field changes as small as biological signals at a distance, known as EPS (Electric Potential Sensing). Various examples of non-contact (or non-ohmic) sensing using EPS include: electrocardiogram (ECG), electromyogram (EMG), and EOG. In various embodiments, a non-contact means of using the EOG for control of a hearing assistance device uses an antenna within each of a pair of hearing aids and ear-to-ear communication. As the wearer's eyes move, one sensor in a first hearing assistance device would trend in the positive direction, the other sensor in a second hearing assistance device would trend in the negative, as the corneas of each eye move toward or away from the sensors. Communication between the hearing assistance devices (left and right, for example) would discern the differential. In one embodiment, one antenna on a single hearing aid is used, and additional steps are added to eliminate artifacts and biologically-induced drift. The present subject matter provides a unique, intuitive interface added to even the smallest of hearing assistance devices, even deep fit invisible units where no external action or medium was previously possible for hearing aid control.

Figure 1B:
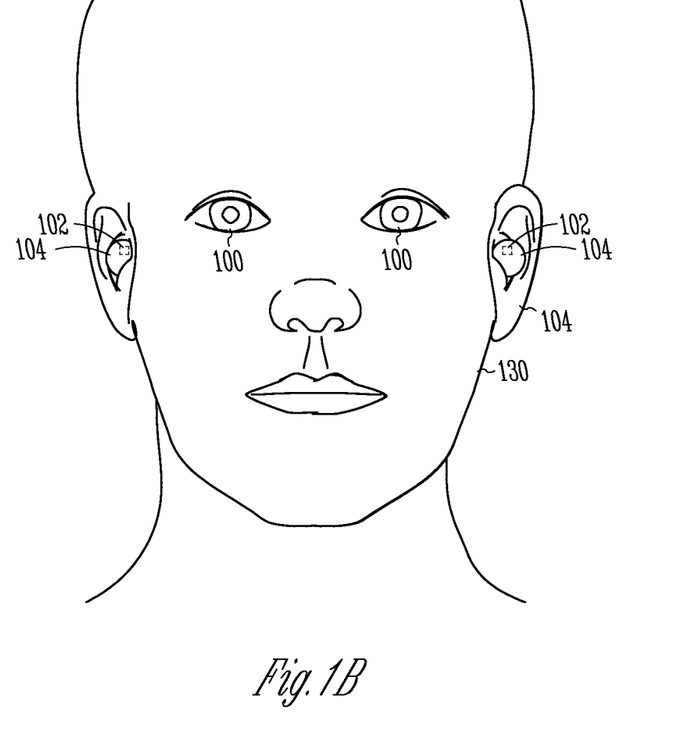
FIG. 1B illustrates a system including a hearing assistance device adapted to be worn by a wearer and used to obtain an EOG, according to various embodiments of the present subject matter.

FIG. 1B illustrates a system including a hearing assistance device adapted to be worn by a wearer and used to obtain an EOG, according to various embodiments of the present subject matter. A wearer 130 has two hearing assistance devices 104, each hearing assistance device having a sensor 102 or electrode on or in the device. The sensors 102 are configured to sense movement of the wearer's eyes 100 to obtain an EOG, in various embodiments.

Figure 1C:
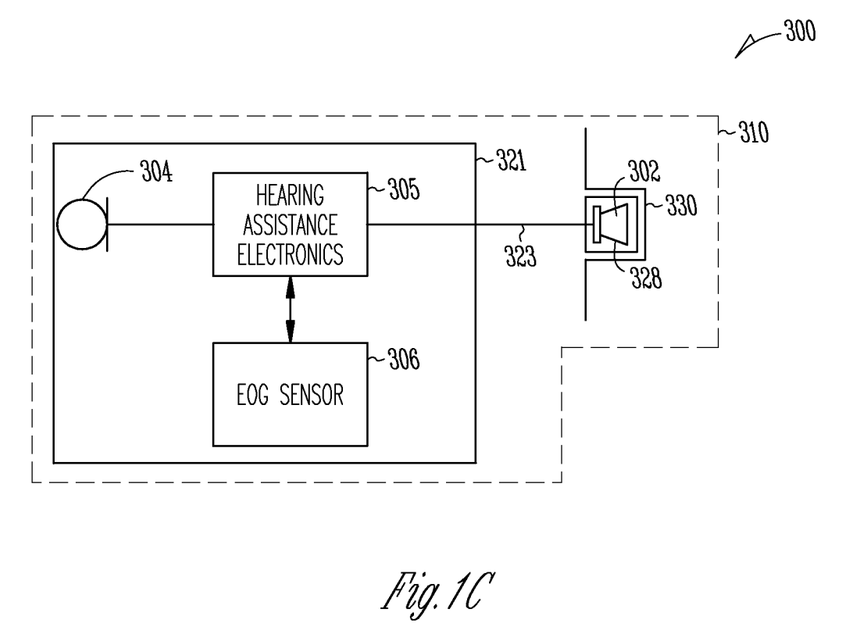
FIG. 1C illustrates a block diagram of a system including a hearing assistance device adapted to be worn by a wearer, according to various embodiments of the present subject matter.

FIG. 1C illustrates a block diagram of a system 300 including a hearing assistance device 310 adapted to be worn by a wearer, according to various embodiments of the present subject matter. In various embodiments, the hearing assistance device 310 includes a first housing 321, an acoustic receiver or speaker 302, positioned in or about the ear canal 330 of a wearer and conductors 323 coupling the receiver (or speaker) 302 to the first housing 321 and the electronics enclosed therein. The electronics enclosed in the first housing 321 includes a microphone 304, hearing assistance electronics 305 and a sensor or electrode 306 for determining an EOG. In various embodiments, the hearing assistance electronics 305 includes at least one processor and memory components. The memory components store program instructions for the at least one processor. The program instructions include functions allowing the processor and other components to process audio received by the microphone 304 and transmit processed audio signals to the speaker 302 in a second housing 328. The speaker emits the processed audio signal as sound in the user's ear canal. In various embodiments, the hearing assistance electronics includes functionality to amplify, filter, limit, condition or a combination thereof, the sounds received using the microphone 304.

Figure 2A:
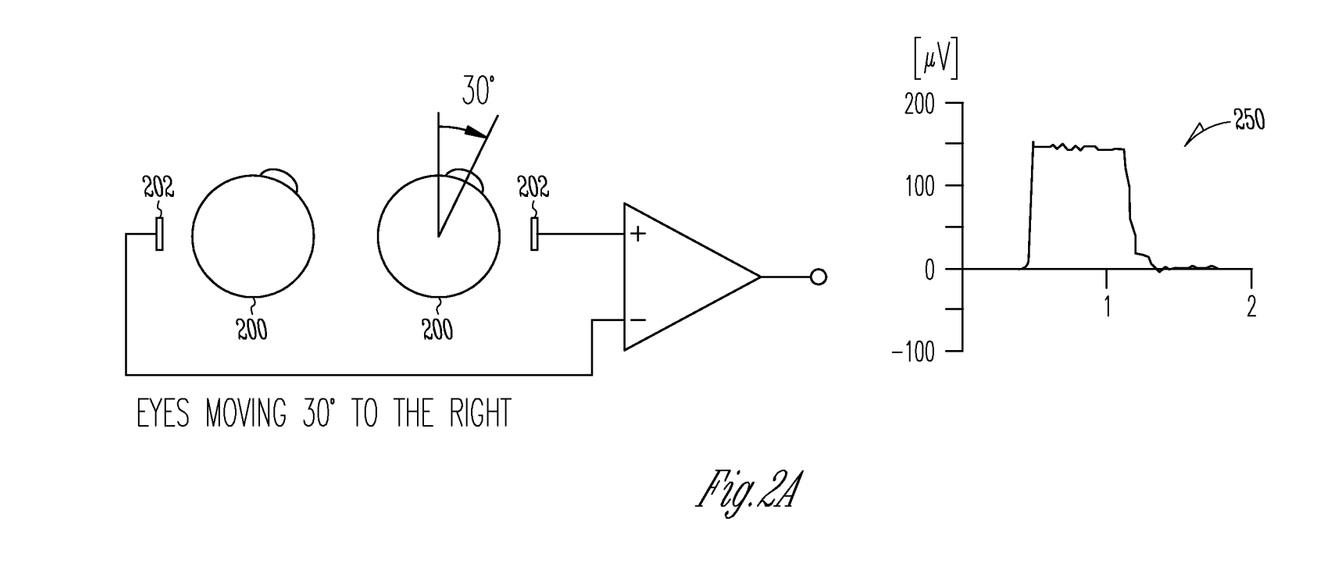
FIGS. 2A-2B illustrate graphical depictions of EOGs based on eye movement, according to various embodiments of the present subject matter.
Figure 2B:
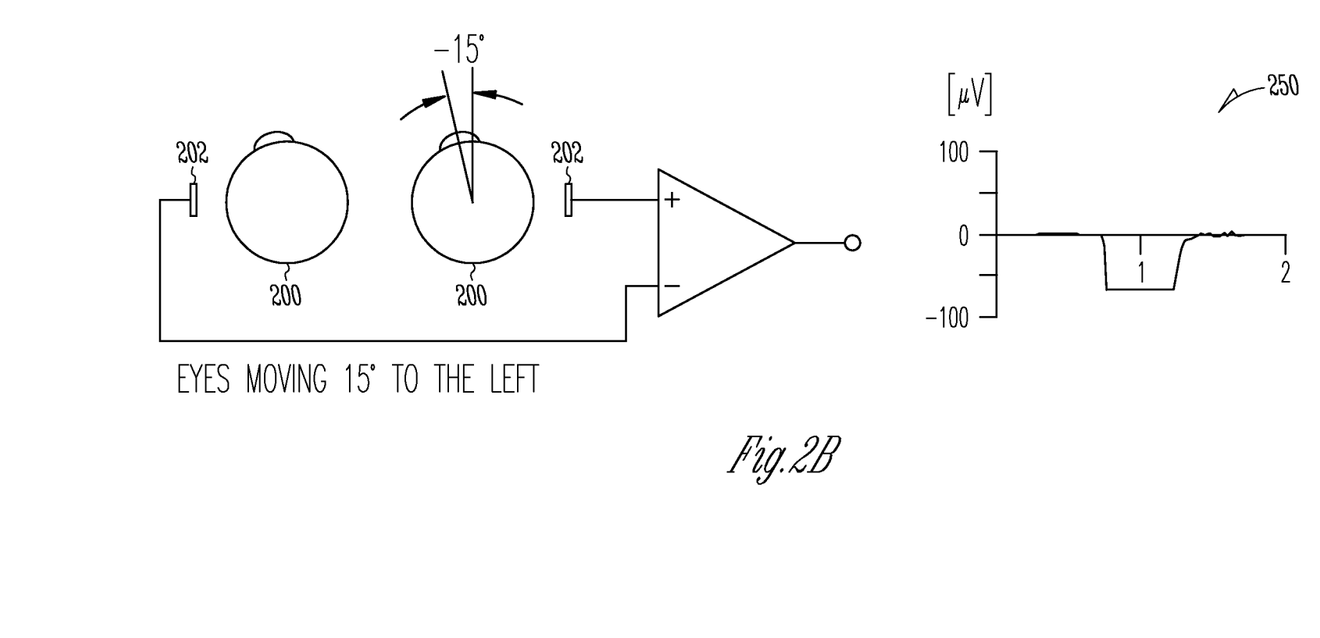

FIGS. 2A-2B illustrate graphical depictions of EOGs based on eye movement, according to various embodiments of the present subject matter. By placing EOG electrodes 202 in the ear canal or on the ear as part of a hearing assistance device, movement of a wearer's eye 200 can be precisely detected and those movements are used to control desired functions of the hearing device. As the wearer looks to the left or the right, the charge shifts in the space between the users ears—a charge that can be detected by appropriate sensors on or in the hearing assistance device. The resulting EOG for each eye movement is shown at 250. In FIG. 2A, the electrodes 202 detect movement of the eye 200 to the right 30 degrees. In FIG. 2B, the electrodes 202 detect movement of the eye 200 to the left 15 degrees.

Figure 3:
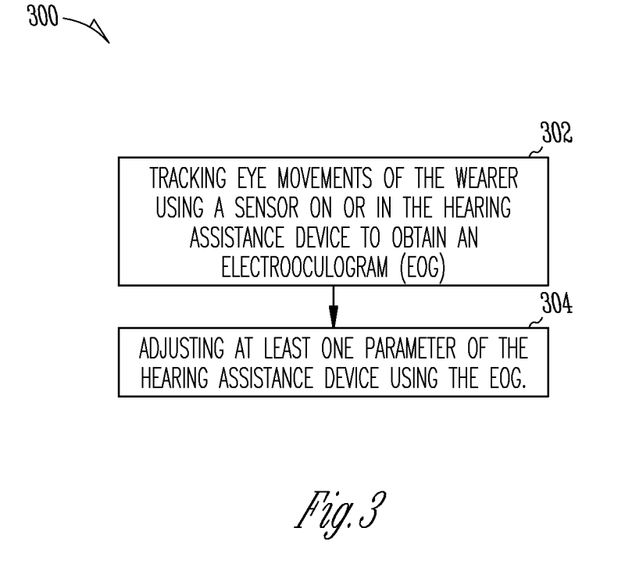
FIG. 3 illustrates a flow diagram of a method of operating a hearing assistance device, according to various embodiments of the present subject matter.

FIG. 3 illustrates a flow diagram of a method of operating a hearing assistance device, according to various embodiments of the present subject matter. One aspect of the present subject matter includes a method 300 of operating a hearing assistance device worn by a wearer. The method includes tracking eye movements of the wearer using an electrode on or in the hearing assistance device to obtain an electrooculogram (EOG), at 302. At 304, at least one parameter of the hearing assistance device is adjusted using the EOG, according to various embodiments.

Various embodiments of the present subject matter support wireless communications with a hearing assistance device. In various embodiments the wireless communications can include standard or nonstandard communications. Some examples of standard wireless communications include link protocols including, but not limited to, Bluetooth™, IEEE 802.11 (wireless LANs), 802.15 (WPANs), 802.16 (WiMAX), ANT, cellular protocols including, but not limited to CDMA and GSM, ZigBee, and ultra-wideband (UWB) technologies. Such protocols support radio frequency communications and some support infrared communications. Although the present system is demonstrated as a radio system, it is possible that other forms of wireless communications can be used such as ultrasonic, optical, and others. It is understood that the standards which can be used include past and present standards. It is also contemplated that future versions of these standards and new future standards may be employed without departing from the scope of the present subject matter.

The wireless communications support a connection from other devices. Such connections include, but are not limited to, one or more mono or stereo connections or digital connections having link protocols including, but not limited to 802.3 (Ethernet), 802.4, 802.5, USB, ATM, Fibre-channel, Firewire or 1394, InfiniBand, or a native streaming interface. In various embodiments, such connections include all past and present link protocols. It is also contemplated that future versions of these protocols and new future standards may be employed without departing from the scope of the present subject matter.

It is understood that variations in communications protocols, antenna configurations, and combinations of components may be employed without departing from the scope of the present subject matter. Hearing assistance devices typically include an enclosure or housing, a microphone, hearing assistance device electronics including processing electronics, and a speaker or receiver. It is understood that in various embodiments the microphone is optional. It is understood that in various embodiments the receiver is optional. Antenna configurations may vary and may be included within an enclosure for the electronics or be external to an enclosure for the electronics. Thus, the examples set forth herein are intended to be demonstrative and not a limiting or exhaustive depiction of variations.

It is further understood that any hearing assistance device may be used without departing from the scope and the devices depicted in the figures are intended to demonstrate the subject matter, but not in a limited, exhaustive, or exclusive sense. It is also understood that the present subject matter can be used with a device designed for use in the right ear or the left ear or both ears of the wearer.

It is understood that the hearing aids referenced in this patent application include a processor. The processor may be a digital signal processor (DSP), microprocessor, microcontroller, other digital logic, or combinations thereof. The processing of signals referenced in this application can be performed using the processor. Processing may be done in the digital domain, the analog domain, or combinations thereof. Processing may be done using subband processing techniques. Processing may be done with frequency domain or time domain approaches. Some processing may involve both frequency and time domain aspects. For brevity, in some examples drawings may omit certain blocks that perform frequency synthesis, frequency analysis, analog-to-digital conversion, digital-to-analog conversion, amplification, and certain types of filtering and processing. In various embodiments the processor is adapted to perform instructions stored in memory which may or may not be explicitly shown. Various types of memory may be used, including volatile and nonvolatile forms of memory. In various embodiments, instructions are performed by the processor to perform a number of signal processing tasks. In such embodiments, analog components are in communication with the processor to perform signal tasks, such as microphone reception, or receiver sound embodiments (i.e., in applications where such transducers are used). In various embodiments, different realizations of the block diagrams, circuits, and processes set forth herein may occur without departing from the scope of the present subject matter.

The present subject matter is demonstrated for hearing assistance devices, including hearing aids, including but not limited to, behind-the-ear (BTE), in-the-ear (ITE), in-the-canal (ITC), receiver-in-canal (RIC), or completely-in-the-canal (CIC) type hearing aids. It is understood that behind-the-ear type hearing aids may include devices that reside substantially behind the ear or over the ear. Such devices may include hearing aids with receivers associated with the electronics portion of the behind-the-ear device, or hearing aids of the type having receivers in the ear canal of the user, including but not limited to receiver-in-canal (RIC) or receiver-in-the-ear (RITE) designs. The present subject matter can also be used in hearing assistance devices generally, such as cochlear implant type hearing devices and such as deep insertion devices having a transducer, such as a receiver or microphone, whether custom fitted, standard, open fitted or occlusive fitted. It is understood that other hearing assistance devices not expressly stated herein may be used in conjunction with the present subject matter.

This application is intended to cover adaptations or variations of the present subject matter. It is to be understood that the above description is intended to be illustrative, and not restrictive. The scope of the present subject matter should be determined with reference to the appended claims, along with the full scope of legal equivalents to which such claims are entitled.

What is claimed is:

1. A method of operating hearing assistance devices worn by a wearer, the method comprising:
   tracking eye movements of the wearer using a first sensor on or in a first hearing assistance device worn in a first ear of the wearer;
   tracking the eye movements using a second sensor on or in a second hearing assistance device worn in a second ear of the wearer;
   using signals from the first and second sensors to obtain an electrooculogram (EOG) using wireless communication between the first and second hearing assistance devices to combine the signals; and
   adjusting at least one parameter of at least one of the first or second hearing assistance device using the EOG.

2. The method of claim 1, wherein tracking eye movements includes using electrodes.

3. The method of claim 1, wherein using signals from the first and second sensors includes discerning a differential between the signals.

4. The method of claim 1, wherein using a sensor includes using an Electric Potential Sensing (EPS) sensor.

5. The method of claim 1, wherein using a sensor includes using an electrode adapted to measure potential.

6. The method of claim 1, wherein using a sensor includes using an antenna configured for non-ohmic sensing.

7. The method of claim 1, wherein each of the first and second hearing assistance devices includes an antenna, and wherein communication between the first and second hearing assistance devices is used to obtain the EOG.

8. The method of claim 1, wherein adjusting at least one parameter of the hearing assistance device includes using a digital signal processor (DSP) in communication with the electrode.

9. The method of claim 1, wherein adjusting at least one parameter of the hearing assistance device includes adjusting volume.

10. The method of claim 1, wherein adjusting at least one parameter of the hearing assistance device includes adjusting directional control.

11. The method of claim 1, wherein adjusting at least one parameter of the hearing assistance device includes adjusting memory presets.

12. The method of claim 1, wherein adjusting at least one parameter of the hearing assistance device includes adjusting beamforming.

13. The method of claim 2, wherein adjusting at least one parameter of the hearing assistance device includes adjusting binaural beamforming.

14. A hearing assistance system for a wearer, comprising:
a first sensor on or in a first hearing assistance device worn in a first ear of the wearer, the first sensor configured to track movements of the wearer's eyes; and
a second sensor on or in a second hearing assistance device worn in a second ear of the wearer, the second sensor configured to track the movements, wherein signals from the first and second sensors are combined using wireless communication between the first and second hearing assistance devices to obtain an electrooculogram (EOG).

15. The system of claim 14, further comprising a controller in the first or second hearing assistance device, the controller configured to adjust at least one parameter of the first or second hearing assistance device using the EOG.

16. The system of claim 15, wherein the controller includes a digital signal processor (DSP).

17. The system of claim 14, wherein at least one of the first or second sensor includes an electrode configured to measure potential.

18. The system of claim 14, wherein at least one of the first or second sensor includes an antenna configured for non-ohmic sensing.

19. The system of claim 14, wherein at least one of the first or second sensor includes an Electric Potential Sensing (EPS) sensor.

20. The system of claim 14, wherein at least one of the first or second hearing assistance device includes a receiver.

21. The system of claim 14, wherein at least one of the first or second hearing assistance device includes a hearing aid.

22. The system of claim 21, wherein the hearing aid includes an in-the-ear (ITE) hearing aid.

23. The system of claim 21, wherein the hearing aid includes a behind-the-ear (BTE) hearing aid.

24. The system of claim 21, wherein the hearing aid includes an in-the-canal (ITC) hearing aid.

25. The system of claim 21, wherein the hearing aid includes a receiver-in-canal (RIC) hearing aid.

26. The system of claim 21, wherein the hearing aid includes a completely-in-the-canal (CIC) hearing aid.

27. The system of claim 21, wherein the hearing aid includes a receiver-in-the-ear (RITE) hearing aid.

\* \* \* \* \*